(12) United States Patent
Bond et al.

(10) Patent No.: US 9,039,663 B2
(45) Date of Patent: May 26, 2015

(54) INTRAVENOUS THERAPY

(76) Inventors: Marian Bond, Melbourne Village, FL (US); Jeffrey R. Schwindt, Indianapolis, IN (US)

(*) Notice: Subject to any disclaimer, the term of this patent is extended or adjusted under 35 U.S.C. 154(b) by 0 days.

(21) Appl. No.: 13/261,582

(22) PCT Filed: Aug. 1, 2011

(86) PCT No.: PCT/US2011/046151
§ 371 (c)(1), (2), (4) Date: Feb. 1, 2013

(87) PCT Pub. No.: WO2012/018738
PCT Pub. Date: Feb. 9, 2012

(65) Prior Publication Data
US 2013/0204189 A1 Aug. 8, 2013

Related U.S. Application Data

(60) Provisional application No. 61/370,051, filed on Aug. 2, 2010.

(51) Int. Cl.
*A61M 25/02* (2006.01)
*A61F 5/30* (2006.01)
*A61B 17/132* (2006.01)

(52) U.S. Cl.
CPC ............ *A61M 25/02* (2013.01); *A61B 17/1322* (2013.01); *A61F 5/30* (2013.01); *A61M 2025/0213* (2013.01); *A61M 2025/0253* (2013.01); *A61M 2025/026* (2013.01)

(58) Field of Classification Search
CPC .......... A61M 25/02; A61M 2025/024; A61M 2025/0246; A61M 2025/026; A61M 2025/0213; A61M 2025/0206; A61M 2025/0253
USPC ........... 604/174–175, 177, 179; 128/877–878
See application file for complete search history.

(56) References Cited

U.S. PATENT DOCUMENTS

| | | | | |
|---|---|---|---|---|
| 3,724,456 A * | 4/1973 | Waxman | ........................ | 128/877 |
| 4,314,568 A * | 2/1982 | Loving | ........................ | 606/201 |
| 4,470,410 A * | 9/1984 | Elliott | ........................ | 128/877 |
| 7,425,206 B2 * | 9/2008 | Byrne et al. | ................... | 604/174 |
| 2005/0076921 A1 * | 4/2005 | Rozier et al. | ................... | 128/877 |
| 2005/0137496 A1 * | 6/2005 | Walsh et al. | ................... | 600/561 |
| 2007/0265572 A1 * | 11/2007 | Smith et al. | ................... | 604/174 |

* cited by examiner

*Primary Examiner* — Aarti B Berdichevsky

(57) ABSTRACT

A medical device is disclosed that can be used to provide a space at an IV catheter site so that kinking of the IV is substantially prevented. The disclosed medical device includes a spacer and an attachment material. The attachment material maybe an elongated strap. The spacer may comprise an elongated member. The elongated strap may be elastomeric and self-adhesive.

17 Claims, 4 Drawing Sheets

INTRAVENOUS THERAPY

CROSS-REFERENCE TO RELATED APPLICATIONS

This application claims the benefit of U.S. Ser. No. 61/370,051 filed Aug. 2, 2010.

BACKGROUND OF INVENTION

The present invention relates to a medical device, and particularly to a medical device that can be used, for example, in the antecubital fossa at the site of an intravenous puncture. More particularly, the present invention relates to a medical device that permits a range of motion in a patient's extremity without kinking the intravenous cannula.

SUMMARY OF INVENTION

In nearly all medical procedures, an intravenous (IV) catheter is inserted in a patient's vein in order to deliver medication, fluids or blood products. Often the antecubital (AC) fossa vein is chosen because the vein is usually large, easy to find, and accommodating of larger IV catheters. Thus, the vein provides an ideal site when large amounts of fluids or caustic medications must be administered—such as in an emergency room (E.R.).

However, the antecubital vein's location in an area of flexion region is a drawback, as bending of the elbow can be uncomfortable to the patient and may occlude the flow of the intravenous solution. Often, the patient's upper extremity flexion will set off IV pump alarms. When IV pump alarms are set off, fluid administration stops and a nurse is typically required to check on the patient, insure that the IV catheter is not compromised, reset the pump alarm, and sometimes reintroduce the IV catheter at a new location. Such circumstances are estimated to draw a nurse or other caretaker away from other duties dozens of times a shift. Interruption of crucial medication administration, such as Heparin and cardiac drips, may be delayed. A patient's recuperative sleep and rest are interrupted by sounding alarms.

The present disclosure relates to one or more of the following features, elements or combinations thereof. Broadly, a medical device is disclosed. The medical device includes a spacer and an attachment material. The attachment material is illustratively an elongated strap. The spacer illustratively comprises an elongated member. The elongated strap may be elastomeric and self-adhesive. In one embodiment, the elongated strap may be used to secure the spacer in place. The medical device can be used to provide a space at an IV catheter site so that kinking of the IV is substantially prevented.

Additional features of the disclosure will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
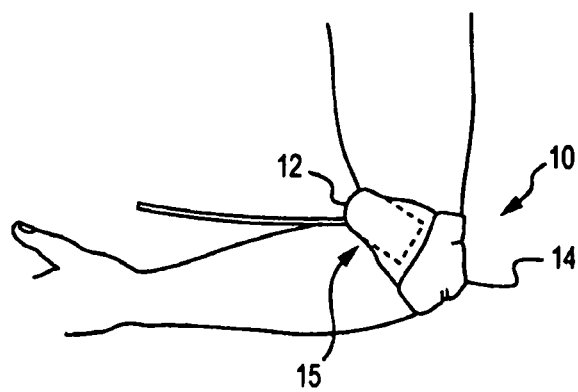
FIG. 1 is a side view of an exemplary embodiment of a medical device according to one embodiment of the present invention.

One embodiment of the present disclosure is shown in FIG. 1, wherein the invention relates broadly to a medical device 10. Medical device 10 may include a spacer 12 and an elongated strap 14 connected to spacer 12. A caretaker may place medical device 10 in the flexor region of the arm, near or over an antecubital IV catheter site, indicated generally by reference number 15. However, it is contemplated herein that such a medical device is not limited to the flexor region of the arm, and may in the alternative be used at other catheter sites on a subject's body.

Figure 2:
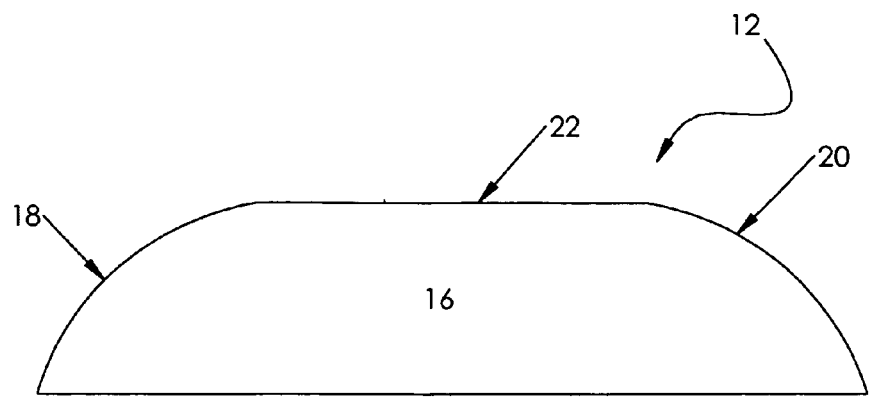
FIG. 2 is a plan view of a spacer according to one embodiment of the present invention.

As can be seen in FIG. 2, spacer 12 is illustratively formed of an elongated, pliable member 16 that has a first end 18 and a second end 20. In one illustrative embodiment, shown in FIG. 2, member 16 is tubular in shape and has a tapered first end 18 and tapered second end 20. By providing tapered ends 18, 20, member 16 can be thicker in the antecubital fossa and thinner at ends 18, 20, so as to not protrude significantly at ends 18, 20. This provides a slimmer profile and less opportunity for interference with other objects where the first and second ends 18, 20 might otherwise dislodge the device. In the alternative, first and second ends 18, 20 may define a smaller diameter than the central portion 22 of member 16.

Figure 3:
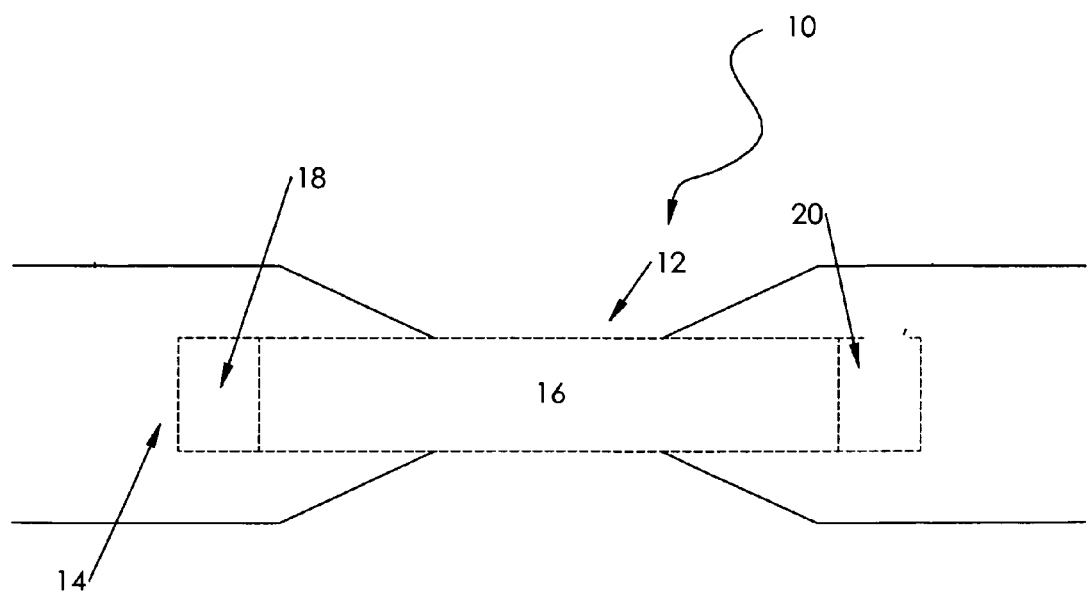
FIG. 3 is a top view of one embodiment of the medical device, showing the spacer of FIG. 2 coupled with an elastomeric material.

As can be seen in FIG. 3, member 16 is illustratively secured to a patient using strap 14. In the embodiment shown, strap 14 has stretchable or elastomeric qualities, such as can be found in, for example, the COBAN™ self-adherent medical-grade wrap available from 3M at http://solutions.3m.com/wps/portal/3M/en US/3MSWC/SkinWound-Care/BrandsDirectory/Coban/. Of course, it is contemplated that other types of straps can be used, and it is not required that strap 14 be longitudinally stretchable. Nonetheless, in the preferred embodiment, such stretchable qualities can combine with self-adhesion properties, such that strap 14 can be used to secure member 16 at an antecubital IV catheter site without the use of further attaching or securing mechanisms.

Figure 4:
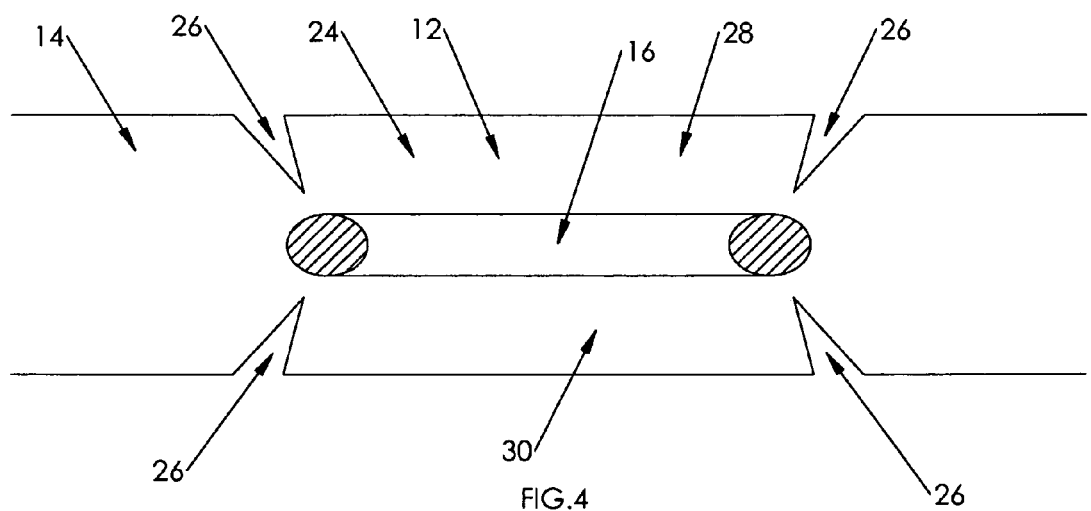
FIG. 4 is a top view of an embodiment of the medical device, showing the construction of the medical device.
Figure 5:
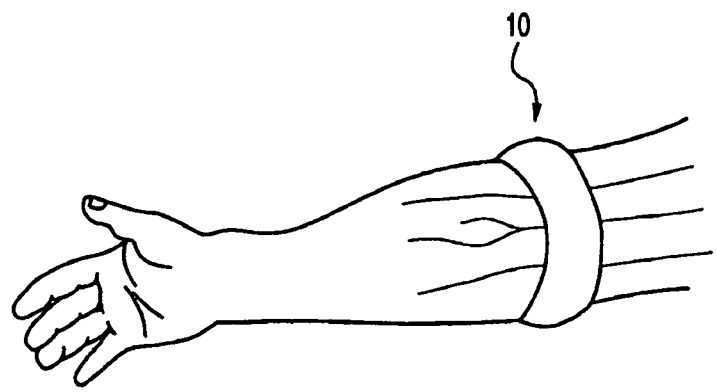
FIG. 5 is a perspective view of the exemplary embodiment of the present invention shown in use.

In one contemplated embodiment, visible in FIG. 4, an approximately three-inch wide strap 14 can be used with a member 16 that is approximately one inch in diameter. This allows a member-enclosing portion 24 of strap 14 to be wrapped around member 16, securing member 16 in position. In the illustrative embodiment, slits 26 are cut in strap 14 so that trapezoidal tabs 28, 30 form opposing tabs of member-enclosing portion 24. In this embodiment, tabs 28, 30 can be wrapped around member 16 so that member 16 is wrapped and secured in place by both tabs 28, 30. Additionally, the trapezoidal shape of tabs 28, 30 allows the corners of tabs 28, 30 to be folded onto and contact strap 14, thereby further securing member 16 in place.

It should be understood that the geometry and dimensions disclosed herein are merely illustrative, and the invention is not limited as such. Other strap 14 dimensions and configurations are possible, as are other configurations and dimensions for member 16. Whatever configuration is used should still accomplish one goal of the medical device 10: providing a space at the IV site that allows the IV catheter to form around the space, rather than kink, when a patient's arm is flexed.

Member 16 may be formed of a material that provides flexibility, yet resilience when placed in the flexor region. For example, the member 16 material should be comfortable enough that a patient can bend his or her arm, but member 16 substantially maintains its shape so that it provides, for example, a radius of curvature about which the IV catheter can bend. With flexion of the upper extremity, the biceps tendon rises. This function further assists one of the intents of the medical device disclosed herein by preventing occlusion of the catheter.

It is contemplated that member 16 can comprise a foam, gel, cloth, sponge, or any other type of material that provides flexibility and resilience. Member 16 may be a single piece, or may be a plurality of pieces that are grouped or held together to form spacer 12, e.g. small spheres. It may alternatively be a combination of materials. In the illustrated embodiment, member 16 is formed to be cylindrical, with tapered ends 18, 20. Member 16 may also be covered with another substance, such as an absorptive material. Various components of device 10 may be anti-microbial, absorptive, and/or may contain topical medicines as desirable for the particular application.

In the illustrated embodiment, a portion of strap 14 functions to attach member 16 to strap 14. However, it is contemplated that other methods may be used to attach member 16 to strap 14. For example, member 16 may be glued, attached with hook-and-loop fasteners, attached with an additional strap, or secured in any other manner known in the art. Strap 14 may also be formed in a tubular shape such that it can house member 16 inside.

In yet another embodiment, a wrap 32 may be used to attach or further secure member 16 to strap 14. In this embodiment, wrap 32 may be, for example, a rectangularly shaped material that can wrap around or through strap 14 as well as member 16. Wrap 32 may include a hook-and-loop fastener that secures wrap 32 to itself, or any other means known in the art. Strap 14 may be designed such that it can be tucked inside wrap 32, such that unnecessary strap material is not left hanging. It is contemplated that wrap 32 may be patterned, colored, or printed with selected designs. For example, wrap 32 may be colored such that different colors signify different embodiments, different sizes, different days of the week (on which device 10 was applied), or merely so that a patient can choose his or her favorite color. Wrap 32 may alternatively have advertising, cartoon characters, or any other type of printed design desirable.

Still other embodiments are contemplated by the present invention. Medical device 10 is contemplated to be disposable, so as to eliminate the need for re-sterilization. However, it may also be possible to have only a portion (e.g. the portion near the IV catheter site) of medical device disposable. Member 16 may be pliable enough to mold around the interior aspect of the AC. The materials used for member 16, strap 14, and any other elements may be numerous. Strap 14 may also be uniformly wider, or become wider at one portion, so as to cup the elbow and provide increased stabilization of the device.

In yet another embodiment, strap 14 may provide a slit that positions around the elbow of the patient. In still another embodiment, strap 14 may have a slit that extends along the majority of strap 14, allowing a caretaker to effectively have a member-enclosing portion 24 that is a single piece, connected to two straps that can be wrapped around the patient. Still another exemplary embodiment of the present invention may be a continuous cylindrical tube of various materials that is elastic enough to conform to the arm and firm enough to maintain space at the IV site without restricting the blood flow. The cylindrical tube may be cut lengthwise into two sections that may be trimmed to an appropriate patient size. The two sections may be rejoined by using a self-adherent or hook-and-loop closure. In yet a further embodiment, the device may be attached to the inner and outer aspects of the elbow by an alcohol released taping material.

Figure 6:
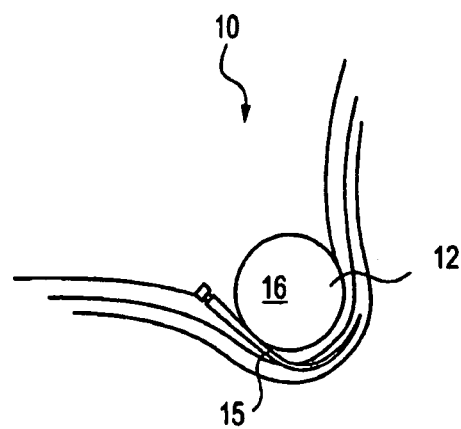
FIG. 6 is the cross sectional view of the exemplary embodiment of the present invention shown in use.

In an exemplary embodiment, shown in FIG. 6, medical device 10 is easily removable from a patient, or at a minimum is movable by a caretaker, so as to permit a caretaker to visualize the IV site 15 several times a day. In order to facilitate repeated access to the IV site, medical device 10 may use the self-adhering material disclosed herein, or may use other quick-release means of closure (not shown in FIG. 6) as known in the art. For example, hook-and-loop closures, medical tape, tooth-embedded fasteners, and other means of closure are within the scope of this invention. Medical device 10 may incorporate into elbow protection to prevent skin sheering when a subject is bedridden. Although it is contemplated that one size will fit nearly all patients, various sizes may be provided as necessary for adults, children or infants.

It is contemplated that in one embodiment, the present invention may enable doctors or nurses to provide continuous IV therapy of medications, drips, and fluids for their patients who have an IV placed in the AC. An exemplary embodiment of the present invention may not be a restraint and the patient's arm may be free for normal use. An exemplary embodiment may be removed for visualization of the site. An IV stabilizer may be used with the present invention due to the comforting cushion it provides. The present invention may prevent unnecessary IV restarts, thus reducing infection. Nursing intervention time when IV therapy is incorporated with a computerized intravenous pump may significantly decrease. The uninterrupted flow of fluids and medications maximizes their therapeutic value.

In another embodiment of the present invention, strap 14 may be trimmed (for example with scissors) to fit arm size. The device may be applied by gently pulling the ends of the elastic banding together and securing the device. In typical applications, a caregiver should be able to fit, for example, two fingers under the banding without noting depression of the cylinder into the AC. It is also contemplated that strap 14 may be overlapped, or doubled-back on itself using a loop.

Finally, it is contemplated that the present invention could be used outside of IV therapy to decrease disruption of circulation in some disease processes, such as carpel tunnel syndrome and Raynaud's disease.

While the disclosure is susceptible to various modifications and alternative forms, specific exemplary embodiments thereof have been shown by way of example in the drawings and have herein been described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

A plurality of advantages arises from the various features of the present disclosure. It will be noted that alternative embodiments of various components of the disclosure may not include all of the features described yet still benefit from at least some of the advantages of such features. Those of ordinary skill in the art may readily devise their own implementations of a medical device that incorporate one or more of the features of the present disclosure and fall within the spirit and scope of the disclosure.

What is claimed is:

1. A medical device for enabling the consistent flow of fluids when an intravenous catheter is placed in an antecubital vein, the medical device comprising: a spacer having a first end and a second end, the spacer comprising a pliable member configured to be positioned near the flexor region of a patient's arm; and an elongated strap connected to the spacer, the strap having a member-enclosing portion configured to hold the member in position over the intravenous catheter site such that the patient is able to flex upper extremities without kinking the intravenous catheter such that the flow of fluids can be consistent through the intravenous catheter while the medical device is in place;

wherein the elongated strap is elastomeric and self-adhesive.

2. The medical device of claim 1, wherein the member has a first end, a second end, and a central portion and the first and second ends are tapered.

3. The medical device of claim 1, wherein the elongated strap is elastomeric in only one direction.

4. The medical device of claim 1, wherein the elongated strap comprises a slit.

5. The medical device of claim 1, wherein the elongated strap has a two trapezoidal tabs that are configured to wrap around the member and secure the member in place on the elongated strap.

6. A medical device for enabling the consistent flow of fluids when an intravenous catheter is placed in an antecubital vein, the medical device comprising: a spacer having a first end and a second end, the spacer comprising a pliable member configured to be positioned near the intravenous catheter site; and an elongated strap connected to the spacer, the strap being configured to hold the member in position substantially over the intravenous catheter site such that the patient is able to flex an extremity without interrupting the flow of intravenous fluid to through the intravenous catheter.

7. The medical device of claim 6, wherein the member has a first end, a second end, and a central portion and the first and second ends are tapered.

8. The medical device of claim 6, wherein the elongated strap is elastomeric and self-adhesive.

9. The medical device of claim 8, wherein the elongated strap is elastomeric in a single direction.

10. The medical device of claim 6, wherein the elongated strap has a two trapezoidal tabs that are configured to wrap around the member and secure the member in place on the elongated strap.

11. A medical device for enabling the consistent flow of fluids when an intravenous catheter is placed in an antecubital vein, the medical device comprising: a pliable member configured to be positioned near the intravenous catheter site; and an elongated strap connected to the pliable member, the strap being configured to hold the member in a curved and arm-conforming position over the intravenous catheter site such that the patient is able to flex an extremity without interrupting the flow of intravenous fluid to through the intravenous catheter.

12. The medical device of claim 11, wherein the member has a first end, a second end, and a central portion and the first and second ends are tapered.

13. The medical device of claim 11, wherein the elongated strap is elastomeric and self-adhesive.

14. The medical device of claim 11, wherein the elongated strap is elastomeric in a single direction.

15. The medical device of claim 11, wherein the elongated strap has a two trapezoidal tabs that are configured to wrap around the member and secure the member in place on the elongated strap.

16. The medical device of claim 11, wherein the spacer comprises a material that maintains a curved space at the anticubital fossa region when the patient flexes the extremity.

17. The medical device of claim 11, wherein the strap comprises a material that can secure the spacer in place while not impeding the blood flow through the patient's extremity.

* * * * *